United States Patent [19]

Mitsui et al.

[11] 4,268,617
[45] May 19, 1981

[54] COLOR PHOTOGRAPHIC LIGHT-SENSITIVE MATERIAL

[75] Inventors: Akio Mitsui; Yoshiaki Suzuki, both of Minami-ashigara, Japan

[73] Assignee: Fuji Photo Film Co., Ltd., Minami-ashigara, Japan

[21] Appl. No.: 79,657

[22] Filed: Sep. 27, 1979

[30] Foreign Application Priority Data

Sep. 27, 1978 [JP] Japan .................. 53-118986

[51] Int. Cl.$^3$ .................. G03C 1/40; G03C 7/00; G03C 5/30; G03C 1/06
[52] U.S. Cl. .................. 430/373; 430/367; 430/377; 430/379; 430/415; 430/447; 430/543; 430/546; 430/559; 430/564; 430/936
[58] Field of Search .............. 430/546, 543, 559, 564, 430/936, 367, 373, 415, 447, 379, 377

[56] References Cited

U.S. PATENT DOCUMENTS 3,847,619 11/1974 Bissonette et al. .................. 430/936
4,002,477 1/1977 Bissonette .................. 430/936

*Primary Examiner*—Richard L. Schilling

*Attorney, Agent, or Firm*—Sughrue, Rothwell, Mion, Zinn and Macpeak

[57] ABSTRACT

A silver halide color photographic light-sensitive material comprising a support and at least one silver halide emulsion layer, at least one of the layers of said photographic sensitive material containing at least one compound selected from the group consisting of those compounds represented by the formulae (I), (II), (III) and (IV):

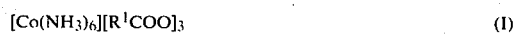

(I)

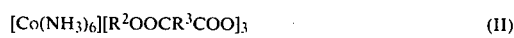

(II)

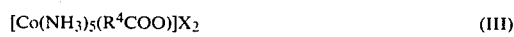

(III)

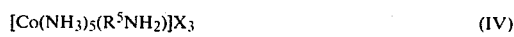

(IV)

wherein $R^1$, $R^2$ and $R^4$ each represent an alkyl group having at least 3 carbon atoms or a fluorine-substituted alkyl group having at least 1 carbon atom; $R^3$ is an alkylene group; $R^5$ is an alkyl group having at least 1 carbon atom; X is a halogen atom, a nitrate ion, a sulfate ion, or a carboxylate ion is disclosed.

20 Claims, No Drawings

COLOR PHOTOGRAPHIC LIGHT-SENSITIVE MATERIAL

BACKGROUND OF THE INVENTION

1. Field of the Invention

This invention relates to a photosensitive material or an image recording material, more particularly, to a photosensitive material or image recording material containing a cobalt complex salt, and a new image forming process employing such photosensitive material or image recording material. More specifically, this invention relates to a color photosensitive material, an image recording material, and a color image forming process.

2. Description of the Prior Art

In the field of color photography to which this invention belongs, a color photographic material which comprises a support which is coated with a silver halide emulsion which has a cyan coupler, a yellow coupler or a magenta coupler contained therein in various manners is imagewise exposed and subjected to a series of processing steps for reproducing an image in the photographic material.

These processing steps generally consist of a color developing step and a desilvering step. In the color developing step the exposed silver halide is reduced with a color developing agent to form silver and the oxidized color developing agent reacts with a coupler to provide a dye image. Thereafter, the color photographic material is transferred to the desilvering step where the silver produced in the color developing step is oxidized with an oxidant (generally referred to as a bleaching agent), and is then dissolved by means of a silver ion chelating agent (which is generally referred to as a fixing agent) and removed from the photographic material. As a result, only a dye image is formed on the photographic material. In practice, the color developing and desilvering steps are accompanied by auxiliary steps for preserving the photographic and physical quality of the image or for improving the stability of the image. These auxiliary steps include the use of a hardening solution for preventing excessive softening of the photosensitive layer under processing, a stop solution for effectively stopping the development reaction, an image stabilizing solution for stabilizing the image, and a solution for removing the anti-halation backing from the support.

A color photographic material processing method of this type has been commonly employed in the industry worldwide since the 1940's. The color photosensitive material used in this color processing usually contains about 1 to 15 g of silver (as silver halide) per 1 m$^2$ of the material. Most reflex image materials typified by a color paper contain 1 to 2.5 g of silver per 1 m$^2$ of the material, whereas most light-sensitive materials for taking photographs such as a color negative film or color reversal film contain 3 to 9 g of silver. While this amount of silver is necessary to provide the desired color image density, a lesser amount would prove a great benefit in terms of saving silver resources as well as processing costs.

One method of reducing the amount of silver halide in the photosensitive material is described in U.S. Pat. Nos. 3,826,652, 3,834,907, 3,856,524, 3,862,842, 3,923,511, 3,970,458 and 4,002,477 wherein the object is achieved by a new color intensification process. According to the specification of the prior art reference, nuclei distributed imagewise serve as a catalyst for oxidation of a cobalt complex compound to form a dye, hence a color image. Since the nuclei are present as a catalyst, only a very small amount of them is used, and therefore, in the case of silver, a far smaller amount of silver salt than is used in a conventional silver salt gelatin emulsion can achieve the desired color density. In this case, the cobalt complex compound is used in forming the imagewise distributed nuclei, more specifically, in an intensifying step following color or black-and-white development. Alternatively if desired, it may be added to the developing solution and used in the nucleus forming step. In the former case, addition of the intensifying step renders the entire processing sequence longer, and in the latter case, the cobalt complex salt remains stable only for a very short period of time in a reducing atmosphere of high pH. Therefore, commercialization of this process requires not only making the processing sequence simple and rapid but also improving the stability of the processing solution.

It is also known in the art of color photography to add a cobalt (III) salt to a silver halide photosensitive material. The addition of a cobalt salt to a photosensitive material as a stabilizer or anti-foggant is disclosed in British Pat. No. 1,214,982, according to which a chelated compound produced by reacting cobalt (II) or manganese (II) with aminopolycarboxylic acid is added to the photosensitive material to thereby prevent fogging and increase the stability of the image. However, the cobalt salt in the British Patent is used in such a small amount it hardly functions as an intensifying agent.

In general, when a large amount of cobalt salt is present in the photosensitive material it considerably lowers sensitivity. Therefore, several methods have been proposed for incorporating a cobalt salt in the photosensitive material such that it exhibits an intensifying effect without causing an excessive decrease in the sensitivity. British Pat. No. 1,456,542 discloses a method of adding a water soluble cobalt (III) complex having as a counter ion, a polyatomic anion like a carbonate ion, a sulfate ion or an acetate ion. U.S. Pat. No. 3,847,619 discloses forming a water insoluble cobalt (III) complex whose ion is a counter ion to the ion of a high molecular weight organic compound and incorporating the complex into a photosensitive material.

Indeed, introducing a cobalt (III) complex into a photosensitive material as a counter ion to the ion of a high molecular weight organic compound is an effective means of containing a high concentration of cobalt (III) complex in the photosensitive material and stabilizing it until the photosensitive material is used. However, as pointed out in British Pat. No. 1,461,892, this process has two defects. The first defect is its inability to limit the decrease in sensitivity to a satisfactorily low level. As is frequently observed, when a strong oxidant such as a water soluble cobalt (III) complex contacts the photosensitive silver halide grains, the latent image speck of silver halide grains formed upon exposure to light, that is the cluster of silver atoms which is produced when the silver halide is reduced by light, is oxidized and destroyed by the cobalt (III) complex. To overcome this defect, the British Pat. No. 1,461,892 discloses a technique in which both the cobalt (III) complex and a tetrazaindene compound are present in the photosensitive material, but the result is not as good as desired and the decrease in sensitivity cannot be held to a commercially acceptable level.

Even if the cobalt complex is contained in a non-sensitive layer free from silver halide, it inevitably adversely affects the photosensitive layer since, as the non-sensitive layer is coated on the photosensitive layer, the complex migrates between the layers with water as a medium and reaches the photosensitive layer. Research Disclosure, Vol. 136, pp. 24–25, No. 13,630, August 1975 describes a method wherein a compound consisting of a water soluble color coupler and a water soluble hexamine cobalt (III) ion as a counter ion for the water soluble color coupler is dispersed in an aqueous solution of gelatin, the resulting dispersion being then added to a silver halide emulsion. This Research Disclosure also reports a method wherein a compound consisting of a color coupler and a hexamine cobalt (III) ion as a counter ion for the color coupler is disclosed in a mixture of triethyl phosphate and di-n-butyl phthalate, the resulting solution is dispersed in an aqueous solution of gelatin, and the dispersion obtained is then added to a silver halide emulsion. However, the cobalt (III) compound is easily dissociated into the cobalt (III) ion and color coupler ion, which are counter ions to each other, and thus fails to limit the decrease in sensitivity to a desirable extent. In addition, the cobalt (III) ion is released from the compound in the initial stage of development and so, it is transferred to the developing solution before completion of the development. As a consequence, only a small intensifying effect is achieved with the cobalt (III) ion. In addition, use of a color coupler, which is a counter ion for the cobalt (III) ion, as an agent to form a color requires addition of the ion paired compound consisting of the cobalt (III) ion and coupler in a light-sensitive layer. Consequently, so long as the method described in Research Disclosure, Vol. 136, pp. 24–25, No. 13,630, August 1965 is employed, the cobalt (III) complex cannot be added to a non-sensitive layer to mitigate any adverse effect due to the cobalt (III) ion of the cobalt (III) complex having the coupler as a counter ion.

The second defect of the process described in British Pat. No. 1,461,892 is that it provides a cobalt (III) complex containing photosensitive material in which photographic properties such as sensitivity deteriorate very easily during storage. It is generally required that a prepared photosensitive material maintain a certain level of photographic properties until use. However, the conventional cobalt (III) complex containing photosensitive material suffers considerable deterioration of its photographic properties during storage, perhaps due to a change in the properties of the silver halide grains or to the change in the cobalt (III) complex as a result of reaction with materials present in the photosensitive material together with said complex. The state of the art is such that none of the methods described in the above references in which a cobalt (III) complex is incorporated in a photosensitive material provides a photosensitive material which retains its photographic properties stably for a normally required period of time.

SUMMARY OF THE INVENTION

It is therefore one object of this invention to provide a silver halide color photographic sensitive material which requires only a low coating weight of silver to give a high color image density.

It is another object of this invention to provide a silver halide color photographic sensitive material containing a cobalt (III) compound which can be added to the silver halide photographic sensitive material in a large amount without causing a great decrease in the sensitive of the photosensitive material or a great change in the photographic characteristics of the sensitive material (such as sensitivity, fogging and contrast) during storage.

It is still another object of this invention to provide a silver halide photographic sensitive material which is prepared by means of a stable oil-in-water emulsion containing a cobalt (III) compound.

These objects of this invention have been accomplished by a silver halide color photographic light-sensitive material comprising a support and at least one silver halide emulsion layer, at least one of the layers of said photographic sensitive material containing at least one compound selected from the group consisting of those compounds which are represented by the formulae (I), (II), (III) and (IV)

$$[Co(NH_3)_6][R^1COO]_3 \qquad (I)$$

$$[Co(NH_3)_6][R^2OOCR^3COO]_3 \qquad (II)$$

$$[Co(NH_3)_5(R^4COO)]X_2 \qquad (III)$$

$$[Co(NH_3)_5(R^5NH_2)]X_3 \qquad (IV)$$

wherein $R^1$, $R^2$ and $R^4$ each represent an alkyl group having at least 3 carbon atoms or a fluorine-substituted alkyl group having at least 1 carbon atom; $R^3$ is an alkylene group; $R^5$ is an alkyl group having at least 1 carbon atom; X is a halogen atom, a nitrate ion, a sulfate ion or a carboxylate ion.

In the formula (I), (II) or (III), the alkyl group represented by $R^1$, $R^2$ and $R^4$ preferably has 3 to 20 carbon atoms, and most preferably 6 to 15 carbon atoms. Such an alkyl group may be straight-chained or branched.

In the formula (I), (II) or (III), the fluorine-substituted alkyl group represented by $R^1$, $R^2$ and $R^4$ preferably has 1 to 20 carbon atoms, most preferably 6 to 12 carbon atoms, and may be straight-chained or branched.

In the formula (II), the alkylene group represented by $R^3$ may be straight or branched and preferably has 1 to 10 carbon atoms, and most preferably it has 1 to 5 carbon atoms. More particularly the alkylene group is preferably a methylene chain having 1 to 10 carbon atoms. Compounds of the formula (II) in which the total number of carbon atoms in $R^2$ and $R^3$ combined is 6 to 12 are most preferred.

In the formula (IV), the alkyl group represented by $R^5$ preferably has 1 to 20 carbon atoms, and may be straight-chained or branched. The alkyl group having 6 to 12 carbon atoms is most preferred.

Preferably X is a halogen atom or a carboxylate ion. The halogen atom represented by X is preferably a chlorine atom or a bromine atom. The carboxylate ion represented by X preferably has 2 to 21 carbon atoms, and it may be substituted with fluorine (e.g., $CH_3COO^-$, $CF_3COO^-$, $C_3F_7COO^-$).

Of the cobalt (III) compounds of the present invention represented by the formulae (I), (II), (III), and (IV), they are preferred in that order.

In one embodiment of this invention, the color photographic sensitive material of this invention is prepared by first dissolving a compound of the formula (I), (II), (III) or (IV) in a high-boiling organic solvent such as tricresyl phosphate or dibutyl phthalate (a low-boiling organic solvent may be used, if desired), then dispersing the solution in an aqueous medium in the presence of a surfactant until an oil-in-water emulsion is obtained whereby the cobalt (III) compound is located in the particles of the oil-in-water emulsion, adding that emulsion to a coupler containing silver halide photographic emulsion which is then coated onto a support (such as cellulose triacetate, polyethylene terephthalate or polyolefin laminated paper). One of the characteristic features of the cobalt (III) compound of this invention having the formula (I), (II), (III) or (IV) is its solubility in an organic solvent, especially a high-boiling organic solvent.

In another embodiment of this invention, the color photographic sensitive material is prepared by incorporating a compound of the formula (I), (II), (III) or (IV) within the particles of an oil-in-water emulsion in a non-sensitive hydrophilic colloid layer adjacent to a coupler containing silver halide emulsion layer.

In still another embodiment of this invention, the color photographic sensitive material is prepared by incorporating a compound of the formula (I), (II), (III) or (IV) within the particles of an oil-in-water emulsion in a non-sensitive hydrophilic colloid layer adjacent to a non-sensitive hydrophilic colloid layer adjacent to the coupler containing silver halide emulsion layer.

Among the above embodiments, from the standpoint of the storage stability of the light-sensitive material it is preferrred to incorporate the cobalt (III) compound non-sensitive hydrophilic colloid layer adjacent a light-sensitive emulsion layer, and particularly preferred to incorporate the cobalt (III) compound in a non-sensitive hydrophilic colloid layer with a non-sensitive hydrophilic colloid layer interposed between the cobalt (III) compound containing layer and the light-sensitive emulsion layer. Further the cobalt (III) compound acts more effectively if it is in a layer located below the silver halide emulsion layer which is to be intensified (i.e., closer to the support). Thus, in accordance with the most preferred embodiment of the present invention, the cobalt (III) compound is present in a hydrophilic colloid layer adjacent and below a hydrophilic colloid layer which is adjacent and below the silver halide emulsion layer to be intensified, and in accordance with the next most preferred embodiment the cobalt (III) compound is present in a hydrophilic colloid layer adjacent and below the silver halide emulsion layer to be intensified.

The silver halide photographic sensitive material according to this invention suffers extremely small decrease in its sensitivity as well as very small change in its photographic characteristics during storage as compared with the conventional cobalt complex containing silver halide photosensitive materials.

These advantages of the photosensitive material containing a cobalt (III) compound according to this invention are presumably due: first, to the high concentration of cobalt (III) compound that can be stably contained in a desired layer of a multi-layer photosensitive material; second, to the high oil-solubility of the complex. The cobalt (III) compound of this invention will not freely migrate through either an aqueous medium or a dried gelatin medium during coating of the emulsion layer or non-sensitive colloidal layer to contact the silver halide grains. Third, the cobalt (III) compound of this invention is dissociated into a cobalt (III) complex ion and an oil-soluble anion within an alkaline developing solution, and the resulting active water soluble cobalt (III) complex ion exhibits high intensifying effect.

For the purpose of preparing the silver halide color photographic sensitive material of this invention, the compound of the formula (I), (II), (III) or (IV) can be incorporated in a gelatin-silver halide emulsion or a hydrophilic colloid by any of the conventional methods such as described in U.S. Pat. Nos. 2,322,027 and 2,533,514, and Japanese Patent Application (OPI) NO. 77211/76. In these conventional methods, an organic compound such as a hydrophobic coupler or hydrophobic U.V. absorbing agent is dissolved in a high-boiling organic solvent such as dibutyl phthalate or tricresyl phosphate, and the resulting solution is dispersed in an aqueous medium in the presence of a surfactant to obtain an emulsion, which is then added to a silver halide emulsion.

The cobalt (III) compound to be used in this invention features coordination of a specific organic ligand to the cobalt (III) ion or a combination of a specific organic counter ion therewith, thus rendering the cobalt (III) compound significantly highly oil soluble. The compound described in Research Disclosure, Vol. 136, pp. 24–25, No. 13,630. August 1975 and wherein the cobalt (III) ion is a counter ion to a water soluble coupler ion more easily dissociates than the compound of this invention having the formula (I), (II), (III) or (IV). Therefore, a photographic sensitive material containing this prior art compound is apt to suffer a decrease in sensitivity due to contact of the cobalt (III) ion with grains of the silver halide emulsion. In addition, the cobalt (III) ion is released into the developing solution in the early stage of development, thus failing to achieve the desired intensifying effect. What is more, the prior art cobalt (III) compound comprises the cobalt (III) ion and coupler ion which are counter ions for each other, and so, invitably both the silver halide emulsion and cobalt (III)-coupler emulsion are contained in the same photosensitive silver halide emulsion layer. Therefore, unlike the cobalt (III) compound of this invention, the conventional cobalt (III) compound cannot be incorporated in a layer adjacent to the coupler containing silver halide emulsion layer (which may be a non-sensitive layer such as the intermediate layer, filter layer, protective layer or antihalation backing, or another photosensitive silver halide emulsion layer) or a layer adjacent to such adjacent layer.

In contrast, the cobalt (III) compound of this invention can be incorporated in a non-sensitive hydrophilic colloid layer separate from the coupler containing sensitive silver halide emulsion layer, and therefore, the particles of the sensitive silver halide emulsion can be isolated from the cobalt (III) ion until development starts, thereby minimizing any change in the photographic characteristics of the sensitive material (a decrease in its sensitivity, or change in sensitivity or gamma during storage) due to the cobalt (III) ion. In accordance with the present invention, due primarily to the high oil-solubility of the cobalt complexes of the present invention, the cobalt complexes can be effectively maintained and retained in the oil particle of an oil-in-water emulsion. Hence, when such an emulsion is dispersed in a hydrophilic colloid such as a silver halide emulsion layer, the compound does not migrate to the silver halide and desensitized it. Generally cobalt complexes can not be incorporated into a photographic material in large amounts because they tend to migrate to the silver halide and desensitize it. In particular, whereas the compound described in the Research Disclosure, supra, dissociates and desensitizes the silver halide, the cobalt compound of the present invention does not.

The compound of this invention having the formula (I), (II), (III) or (IV) is preferably contained in the photosensitive material in an amount in the range of from about 0.01 mol to about 10 mol, more preferably from about 0.1 mol to about 5 mols, per mol of silver contained in the emulsion layer to be intensified of the photosensitive material.

The color photographic sensitive material according to this invention contains a coupler of at least about 50 mol% excess, preferably about 100 mol% excess, of the amount stoichiometrically required based on silver.

The color photographic sensitive material according to this invention contains a silver halide in an amount less than about 1 g/m$^2$, preferably from about 0.4 g/m$^2$ to 0.02 g/m$^2$, per silver halide emulsion layer.

Exemplary unsubstituted alkyl groups represented by $R^1$, $R^2$, $R^4$ or $R^5$ of the formula (I), (II), (III) or (IV) according to this invention are $C_3H_7$—, (n) $C_4H_9$—, (t) $C_4H_9$—, (t) $C_5H_{11}$—, (n) $C_6H_{13}$—, (n) $C_7H_{15}$—, (t) $C_8H_{17}$—, (n) $C_9H_{19}$—, (n) $C_{10}H_{21}$—, (n) $C_{11}H_{23}$—, (n) $C_{12}H_{25}$—, (n) $C_{13}H_{27}$—, (n) $C_{14}H_{29}$—, (n) $C_{15}H_{31}$—, etc.

Exemplary alkylene groups represented by $R^3$ of the formula (II) are —$CH_2$—, —$C_2H_4$—, —$C_3H_6$—, —$C_4H_8$—, —$C_5H_{10}$—, etc.

The fluorine-substituted alkyl group represented by $R^1$, $R^2$ or $R^4$ of the formula (I), (II) or (III) of this invention may have part or all of the hydrogen atoms of the alkyl group substituted with a fluorine atom or atoms. Examples of such alkyl group include the following: $H(CF_2)$—, $H(C_2F_4)$—, $H(C_3F_6)$—, $H(C_4F_6)$—, $H(C_5F_{10})$—, $H(C_6H_{12})$—, $H(C_7F_{14})$—, $H(C_8F_{16})$—, $H(C_9F_{18})$—, $H(C_{10}F_{20})$—, $H(C_{11}F_{22})$—, $H(C_{12}F_{24})$—, $H(C_{13}F_{26})$—, $H(C_{14}F_{28})$—, $H(C_{15}F_{30})$—, $CF_3$—, $C_2F_5$—, $C_3F_7$—, $C_4F_9$—, $C_5F_{11}$—, $C_6F_{13}$—, $C_7F_{15}$—, $C_8F_{17}$—, $C_9F_{19}$—, $C_{10}F_{21}$—, $C_{11}F_{23}$—, $C_{12}F_{25}$—, $C_{13}F_{27}$—, $C_{14}F_{29}$—, $C_{15}F_{31}$—.

Exemplary preferred compounds of this invention are set forth below.

| Compounds of the formula (I): | |
|---|---|
| I-1 | [Co(NH$_3$)$_6$][CF$_3$COO]$_3$ |
| I-2 | [Co(NH$_3$)$_6$][HC$_6$F$_{12}$COO]$_3$ |
| I-3 | [Co(NH$_3$)$_6$][HC$_{11}$F$_{22}$COO]$_3$ |
| I-4 | [Co(NH$_3$)$_6$][HC$_{15}$F$_{30}$COO]$_3$ |
| I-5 | [Co(NH$_3$)$_6$][(n)C$_7$F$_{15}$COO]$_3$ |
| I-6 | [Co(NH$_3$)$_6$][HC$_{10}$F$_{20}$COO]$_3$ |
| I-7 | [Co(NH$_3$)$_6$][C$_{11}$H$_{23}$COO]$_3$ |
| I-8 | [Co(NH$_3$)$_6$][C$_3$F$_7$COO]$_3$ |
| Compounds of the formula (II): | |
| II-1 | [Co(NH$_3$)$_6$][HC$_2$F$_4$CH$_2$O$_2$C(CH$_2$)$_2$COO]$_3$ |
| II-2 | [Co(NH$_3$)$_6$][C$_2$H$_5$O$_2$C(CH$_2$)$_2$COO]$_3$ |
| II-3 | [Co(NH$_3$)$_6$][HC$_6$F$_{12}$CH$_2$O$_2$C(CH$_2$)$_2$COO]$_3$ |
| II-4 | [Co(NH$_3$)$_6$][HC$_4$F$_8$CH$_2$O$_2$C(CH$_2$)$_2$COO]$_3$ |
| Compounds of the formula (III): | |
| III-1 | [Co(NH$_3$)$_5$(CF$_3$COO)]Cl$_2$ |
| III-2 | [Co(NH$_3$)$_5$(HC$_{11}$F$_{22}$COO)]Cl$_2$ |
| III-3 | [Co(NH$_3$)$_5$(HC$_6$F$_{12}$COO)]Cl$_2$ |
| III-4 | [Co(NH$_3$)$_5$(HC$_{15}$F$_{30}$COO)]Cl$_2$ |
| III-5 | [Co(NH$_3$)$_5$(CH$_3$CO$_2$)]SO$_4$ |
| III-6 | [Co(NH$_3$)$_5$(CH$_3$COO)][CH$_3$COO]$_2$ |
| III-7 | [Co(NH$_3$)$_5$(CH$_3$COO)][CF$_3$COO]$_2$ |
| III-8 | [Co(NH$_3$)$_5$(CH$_3$COO)][C$_3$F$_7$COO]$_2$ |
| III-9 | [Co(NH$_3$)$_5$(CH$_3$COO)][H(C$_2$F$_4$)$_3$COO]$_2$ |
| Compounds of the formula (IV): | |
| IV-1 | [Co(NH$_3$)$_5$(n-C$_4$H$_9$NH$_2$)](NO$_3$)$_3$ |
| IV-2 | [Co(NH$_3$)$_5$(n-C$_{16}$H$_{33}$NH$_2$)](NO$_3$)$_3$ |
| IV-3 | [Co(NH$_3$)$_5$(n-C$_{16}$H$_{33}$NH$_2$)]$_2$(SO$_4$)$_3$ |
| IV-4 | [Co(NH$_3$)$_5$(n-C$_8$H$_{17}$NH$_2$)]Cl$_3$ |
| IV-5 | [Co(NH$_3$)$_5$(n-C$_4$H$_9$NH$_2$)][CH$_3$COO]$_3$ |
| IV-6 | [Co(NH$_3$)$_5$(n-C$_4$H$_9$NH$_2$)][CF$_3$COO]$_3$ |
| IV-7 | [Co(NH$_3$)$_5$(n-C$_4$H$_9$NH$_2$)][C$_3$F$_7$COO]$_3$ |
| IV-8 | [Co(NH$_3$)$_5$(n-C$_{16}$H$_{33}$NH$_2$)][CF$_3$COO]$_3$ |

The cobalt compound used in this invention can generally be synthesized by the following method:

A sulfate or chloride of a hexamine cobalt complex is dissolved in water to form an aqueous solution, which is mixed with an aqueous solution having dissolved therein both about 3 mols of aliphatic carboxylic acid or fluoroaliphatic carboxylic acid per mol of the cobalt complex and an approximately equivalent amount of barium hydroxide or sodium hydroxide. The precipitate is separated from the solution, washed with water and dried to provide the oil soluble hexamine cobalt compound of this invention.

Specific examples of the method of synthesizing the oil soluble cobalt compound of this invention will be hereunder described.

SYNTHESIS EXAMPLE 1

Synthesis of compound I-5:

4.73 g of Ba(OH)$_2$.8H$_2$O and 14 g of C$_7$F$_{15}$COOH were thoroughly dissolved in 50 ml of water. To the resulting aqueous solution was added an aqueous solution comprising 3.5 g of [Co(NH$_3$)$_6$]$_2$(SO$_4$)$_3$ dissolved in 40 ml of water. The precipitate was filtered out, washed with water, and dried to provide 16 g of [Co(NH$_3$)$_6$](C$_7$F$_{15}$COO)$_3$.

SYNTHESIS EXAMPLE 2

Synthesis of compound I-8:

2.5 g of NaOH was dissolved in 80 ml of water, to which was further added 12.84 g of C$_3$F$_7$COOH and thoroughly mixed to form a uniform solution. A solution comprising 5.34 g of [Co(NH$_3$)$_6$]Cl$_3$ dissolved in 80 ml of water was added to the resulting aqueous solution under stirring at room temperature. After stirring for additional 30 minutes, the complex precipitate was filtered out, washed with water and dried to provide 14 g of [Co(NH$_3$)$_6$](C$_3$F$_7$COO)$_3$.

SYNTHESIS EXAMPLE 3

Synthesis of compound II-1:

7 g of HC$_2$F$_4$CH$_2$O$_2$C(CH$_2$)$_2$COOH and 1.2 g of NaOH were thoroughly dissolved in 50 ml of water. Another solution were prepared by dissolving 2.7 g of [Co(NH$_3$)$_6$]Cl$_3$ in 50 ml of water, and mixed with the previously prepared aqueous solution of sodium carboxylate under stirring at room temperature. The product was the precipitate of compound II-1 which was washed with water and air-dried to yield 7 g of the end compound.

SYNTHESIS EXAMPLE 4

Synthesis of compound III-5:

5 g of [Co(NH$_3$)$_5$CO$_3$]$_2$SO$_4$ were suspended in 15 ml of water. The suspension was mixed with 12 g of acetic acid and concentrated by heating on a water bath. In about 1.5 hours, a red precipitate formed, which was filtered, washed with cold water and air dried.

SYNTHESIS EXAMPLE 5

Synthesis of Compound III-7:

30 g of the compound III-5 [Co(NH$_3$)$_5$(CH$_3$COO)]SO$_4$ were dissolved in 300 ml of water. Another solution was prepared by dissolving 17.1 g of Ba(OH)$_2$ in 200 ml of water, which was added 11.4 g of CF$_3$COOH under thorough stirring. The resulting aqueous solution was added to the previously prepared aqueous solution of cobalt salt under stirring at room temperature, and the resultant white precipitate was centrifuged. Water was distilled off the supernatant, and the residue was recrystallized from methanol.

SYNTHESIS EXAMPLE 6

Synthesis of compound IV-6:

4.4 g of [Co(NH$_3$)$_5$(nC$_4$H$_9$NH$_2$)]$_2$(SO$_4$)$_3$ synthesized in accordance with the method of J. Brigand, described in C.R. Acad. Sci. (Paris) 225, 1319 (1947) was dissolved in 100 ml of water at 50° C. Another aqueous solution was prepared by dissolving 5.2 g of Ba(OH)$_2$ in 80 ml of water, in which was further dissolved 3.5 g of CF$_3$COOH. The resulting aqueous solution was mixed with the previously prepared aqueous Co salt solution, and the resulting white precipitate was centrifuged. Water was distilled off the supernatant, and the residue was recrystallized from ethanol.

The oil soluble cobalt (III) compound used in this invention is dissolved in an organic solvent, and the solution is dispersed in an aqueous medium in the presence of a surfactant to provide an emulsion which can be incorporated in the silver halide emulsion layer or a hydrophilic colloid layer other than the silver halide emulsion layer. The oil soluble cobalt (III) compound of this invention is preferably dissolved in a high boiling organic solvent which boils at about 180° C. or higher, or a low boiling organic solvent which boils at a temperature in the range of from about 30° C. to 150° C., or a water miscible organic solvent. These organic solvents may be used independently or as a mixture. Examples of the high boiling organic solvent that is preferably used in this invention include: di-n-butyl phthalate, benzyl phthalate, triphenyl phosphate, tri-o-cresyl phosphate, diphenyl mono-p-tert-butylphenyl phosphate, monophenyl di-p-tert-butylphenyl phosphate, diphenyl mono-o-chlorophenyl phosphate, monophenyl di-o-chlorophenyl phosphate, 2,4-di-n-amyl phenol, 2,4-di-t-amyl phenol, N,N-diethyl lauramide, and trioctyl phosphate and trihexyl phosphate of the type described in U.S. Pat. No. 3,676,137.

In addition to these high boiling organic solvents, low boiling and water soluble solvents can also advantageously be used in this invention. They are disclosed in, for example, in U.S. Pat. Nos. 2,801,171; 2,801,170 and 2,949,360 and include:

(1) Substantially water insoluble low boiling organic solvents such as methyl acetate, ethyl acetate, propyl acetate and butyl acetate, isopropyl acetate, ethyl propionate, sec-butyl alcohol, ethyl formate, butyl formate, nitromethane, nitroethane, carbon tetrachloride and chloroform; and (2) Water soluble organic solvents such as methyl isobutyl ketone, β-ethoxyethyl acetate, β-butoxytetrahydrofurfuryl adipate, diethylene glycol monoacetate, methoxytriglycol acetate, acetonylacetone, diacetone alcohol, ethylene glycol, diethylene glycol, dipropylene glycol, acetone, methanol, ethanol, acetonitrile, dimethylformamide, and dioxane.

The silver halide that can be used in the photographic emulsion layer of the photographic sensitive material of this invention is any of silver bromide, silver iodobromide, silver iodochlorobromide, silver chlorobromide and silver chloride. Preferred silver halides are silver chlorobromide, silver iodobromide or iodochlorobromide containing less than 10 mol% of silver iodide.

While there is no particular limitation on the average size of the silver halide grains in the photographic emulsion (for a spherical grain or a grain approximated by a sphere, its average diameter is its grain size, and for a cubic grain, the length of one of its sides is its grain size which is averaged on the basis of the projected area), a grain size less than 3μ is preferred. A grain size less than 2μ is more preferred, and a grain size less than 1.5μ is most preferred.

The grain size distribution may either be narrow or wide.

The silver halide grains in the photographic emulsion may be a regular crystal such as a cube or octagon, or they may be an irregular crystal such as a spherical or platy crystal, or they may be a modification of these crystal. Alternatively, they may comprise a mixture of grains of various crystals.

Each silver halide grain comprises an inner portion and a surface layer which are of different phases or a homogeneous phase. The grain may be such that it forms a latent image mainly on the surface, or it may be such that the latent image is formed mainly within the grain.

The photographic emulsion used in this invention can be prepared by any of the conventional methods such as those described in Chimie et Physique Photographique, by P. Glafkides, Paul Montel, 1967; Photographic Emulsion Chemistry, by G. F. Duffin, The Focal Press, 1966; and Making and Coating Photographic Emulsion, by V. L. Zelikman et al., The Focal Press, 1964. Therefore, any prior art method such as the acid process, neutral process or ammonia process may be used. A soluble silver salt is reacted with a soluble halogen salt by any suitable method such as one-side mixing, simultaneous mixing or a combination thereof.

A method which is generally referred to as the "reverse mixing" may be employed wherein grains are formed in the presence of excess silver ion. One suitable type of simultaneous mixing is what we call the "controlled double jet process" wherein the pAg in the liquid phase where silver halide is formed is maintained at a constant level. This process provides a silver halide emulsion comprising uniform-size grains having a regular crystal. It is to be understood that the silver halide emulsion to be used in this invention may comprise two or more kinds of emulsion that have been prepared separately.

Silver halide grains may be formed or physically ripened in the presence of a cadmium salt, zinc salt, lead salt, thallium salt, iridium salt or a complex salt thereof, rhodium salt or a complex salt thereof, or iron salt or iron complex salt.

After precipitation or physical ripening, the emulsion is usually deprived of the soluble salt it contains by means of the long known "Nudel water washing" following gelation of gelatin, or the flocculation process which uses an inorganic salt comprising polyvalent anion such as sodium sulfate, an anionic surfactant, an anionic polymer (such as polystyrene sulfonic acid), or a gelatin derivative (such as aliphatic acylated gelatin, aromatic acylated gelatin, or aromatic carbamoylated gelatin). Removal of the soluble salt may be omitted.

The silver halide emulsion may be a "primitive" emulsion which has not been chemically sensitized, but generally it is chemically sensitized. Chemical sensitization is performed by any of the methods described in the above cited books of Glafkides and Zelikman et al, and in Die Grundlagen der photographischen Prozesse mit Silberhalogeniden, ed. by H. Frieser, Akademische Verlagsgesellschaft, 1968.

According to these methods, the sulfur sensitization using a compound or activated gelatin that contains sulfur reactive with silver ion, the reduction sensitization using a reductive substance, and the noble metal sensitization using a noble metal such as gold are employed independently or in combination. Preferred sulfur sensitizers are thiosulfate, thioureas, thiazoles, rhodanines and other compounds which are specifically exemplified in U.S. Pat. Nos. 1,574,944; 2,410,689; 2,278,947; 2,728,668; and 3,656,955. Preferred reduction sensitizers are stannous salt, amines, hydrazine derivative, formamidine sulfinic acid, and silane compound which are specifically described in U.S. Pat. Nos. 2,487,850; 2,419,974; 2,518,698; 2,983,609; 2,983,610; and 2,694,637. For the noble metal sensitization, a gold complex salt as well as complex salts of the metals of the Group VIII of the periodic table such as platinum, iridium and palladium can be used, and their specific examples are described in U.S. Pat. Nos. 2,399,083; 2,448,060; and British Pat. No. 618,061.

While the binder or protective colloid to be incorporated in the photographic emulsion is advantageously gelatin, it is to be understood that other hydrophilic colloids may be employed. For instance, proteins such as a gelatin derivative, graft polymer which has gelatin grafted with other polymers, albumin and casein; cellulose derivatives such as hydroxyethyl cellulose, carboxymethyl cellulose and cellulose sulfate ester; sugar derivatives such as sodium alginate and starch derivatives; synthetic hydrophilic homopolymers or copolymers such as polyvinyl alcohol, polyvinyl acetal (partial), poly-N-vinyl pyrrolidone, polyacrylic acid, polymethacrylic acid, polyacrylamide, polyvinyl imidazole and polyvinyl pyrazole.

Preferred gelatins are lime treated gelatin, acid treated gelatin and enzyme treated gelatin of the type described in Bull. Soc. Sci. Phot. Japan, No. 16, page 30, 1966. Hydrolyzed gelatin or enzyme-treated gelatin can also be used. Preferred gelatin derivatives are those obtained by reacting gelatin with various compounds such as acid halides, acid anhydrides, isocyanates, bromoacetic acids, alkane sultones, vinylsulfonamides, maleinimide compounds, polyalkylene oxide and epoxy compounds. Specific examples of the gelatin derivatives are described in U.S. Pat. Nos. 2,614,928; 3,132,945; 3,186,846; 3,312,553; British Pat. Nos. 861,414; 1,033,189; 1,005,784; and Japanese Patent Publication No. 26845/67.

Suitable gelatin graft polymers are those which have gelatin grafted with homo- or copolymers of acrylic acid, methacrylic acid or their esters or acid amides, or vinyl monomers such as acrylonitrile and styrene. Preferred are those graft polymers wherein gelatin is grafted with a polymer somewhat miscible with gelatin such as polyacrylic acid, polymethacrylic acid, polyacrylamide, polymethacrylic acid, polyacrylamide, polymethacrylamide, polyhydroxyalkyl methacrylate.

Examples of these graft polymers are described in U.S. Pat. Nos. 2,763,625; 2,831,767; and 2,956,884.

Typical examples of the synthetic hydrophilic polymers are described in, for instance, West German Patent Application (OLS) No. 2,312,608; U.S. Pat. Nos. 3,620,751 and 3,879,205; Japanese Patent Publication No. 7561/68.

The photographic emulsion used in this invention may be spectrally sensitized by a suitable methine dye and other dyes. Applicable dyes include a cyanine dye, merocyanine dye, complex cyanine dye, complex merocyanine dye, holopolar cyanine dye, hemicyanine dye, styryl dye and hemioxonol dye. Particularly advantageous dyes are those which belong to a cyanine dye, merocyanine dye and complex merocyanine dye. Any of the nuclei commonly used for cyanine dyes as a basic heterocyclic nucleus can be applied to these dyes. To be more specific, a pyrroline, oxazoline nucleus, thiazoline nucleus, pyrrole nucleus, oxazole nucleus, thiazole nucleus, selenazole nucleus, imidazole nucleus, tetrazole nucleus and pyridine nucleus; nuclei having these nuclei fused with an alicyclic hydrocarbon ring; nuclei having these nuclei fused with an aromatic hydrocarbon ring, such as an indolenine nucleus, benzindolenine nucleus, indole nucleus, benzoxazole nucleus, naphthoxazole nucleus, benzothiazole nucleus, naphthothiazole nucleus, benzoselenazole nucleus, benzimidazole nucleus and quinoline nucleus. These nuclei may be substituted at a carbon atom.

As a nucleus having the ketomethylene structure, 5- or 6-membered heterocyclic nuclei such as pyrazoline-5-one nucleus, thiohydantoin nucleus, 2-thioxazolidine-2,4-dione nucleus, thiazolidine-2,4-dione nucleus, rhodanine nucleus and thiobarbituric acid nucleus can be applied to the merocyanine or complex merocyanine dye.

Exemplary useful sensitizing dyes are described in, for example, West German Pat. No. 929,080, U.S. Pat. Nos. 2,231,658; 2,493,748; 2,503,776; 2,519,001; 2,912,329; 3,656,959; 3,672,897; 3,694,217; British Pat. No. 1,242,588; Japanese Patent Publication No. 14030/69.

These sensitizing dyes may be used independently or in combination. Combinations of sensitization, as is typical are illustrated in U.S. Pat. Nos. 2,688,545; 2,977,229; 3,397,060; 3,522,052; 3,527,641; 3,617,293; 3,628,964; 3,666,480; 3,670,428; 3,703,377; 3,769,428; 3,703,377; 3,769,301; 3,814,609; 3,837,862; British Pat. No. 1,344,281; Japanese Pat. Publication No. 4936/68.

The photographic emulsion used in this invention may additionally contain a dye which is incapable of spectral sensitization or a substance which substantially does not absorb visible light and is capable of intensified sensitization. Examples of such additional dye or substance are an amino stilbene compound substituted with a nitrogen containing heterocyclic group (such as those disclosed in U.S. Pat. Nos. 2,933,390; 3,635,721), an aromatic organic acid/formaldehyde condensate (such as those disclosed in U.S. Pat. No. 3,743,510), a cadmium salt and azaindene compound. Particularly useful combinations are described in U.S. Pat. Nos. 3,615,613, 3,615,641; 3,617,295; 3,635,721;

The color photographic sensitive material of this invention can be produced by using a coupler which is generally well known in the art that reacts with the oxidation product of the aromatic amine (usually, a primary amine) developing agent to form a dye. A non-diffusible coupler is desired which has a hydrophobic "ballast" group in the molecule. The coupler is either 4-equivalent or 2-equivalent with respect to the silver ion. A colored coupler capable of color correction or a "DIR coupler" which releases the development inhibitor as the development proceeds may also be used. A coupler of the type that provides a colorless product as a result of coupling reaction may also be used.

A suitable yellow color forming coupler is any of the conventional open-ring ketomethylenic couplers. Benzoyl acetanilide compounds and pivaloyl acetanilide compounds are advantageously used. Specific examples of the suitable yellow color forming coupler are described in U.S. Pat. Nos. 2,875,057; 3,265,506; 3,408,194; 3,551,155; 3,582,322; 3,725,072; 3,891,445; West German Pat. No. 1,547,868; West German Patent Publication Disclosure Nos. 2,219,917, 2,261,361; 2,414,006; British Patent No. 1,425,020; Japanese Patent Publication No. 10738/76; Japanese Patent Public Disclosure Nos. 26133/72; 73147/73; 102636/76; 6341/75; 123342/75; 130442/75; 21827/76; and 87650/75.

Suitable magneta color forming couplers are a pyrazolone compound, an indazolone compound and a cyanoacetyl compound. The pyrazolone compound is advantageously used. Specific examples of the suitable magenta color forming coupler are described in U.S. Pat. Nos. 2,600,788; 2,983,608; 3,062,653; 3,127,269; 3,311,476; 3,419,391; 3,519,429; 3,558,319; 3,582,322; 3,615,506; 3,834,908; 3,891,445; West German Pat. No. 1,810,464; West German Patent Application (OLS) Nos. 2,408,665; 2,417,945; 2,418,595; 2,424,467; Japanese Patent Publication Nos. 6031/65; 45990/76; Japanese Patent Public Disclosure Nos. 20826/76; 58922/77; 129538/74; 74027/74; 159336/75; 42121/77; 74028/74; 60233/75; and 26541/76.

Suitable cyan color forming couplers are a phenolic compound and a naphthol compound. Specific examples of the suitable cyan color forming coupler are described in U.S. Pat. Nos. 2,369,929; 2,434,272; 2,474,293; 2,521,908; 2,895,826; 3,034,892; 3,311,476; 3,458,315; 3,476,563; 3,583,971; 3,591,383; 3,767,411; 4,004,929; West German Patent Application (OLS) Nos. 2,414,830; 2,454,329; Japanese Patent Public Disclosure Nos. 59838/73; 26034/76; 5055/73; and 146828/76.

Examples of the suitable colored coupler are described in such prior art reference as U.S. Pat. Nos. 3,476,560; 2,521,908; 3,034,892; Japanese Patent Publication Nos. 2016/69; 22335/63; 11304/67; 32461/69; Japanese Patent Publication Nos. 2016/69; 22335/63; 11304/67; 32461/69; Japanese Patent Public Disclosure Nos. 26034/76; 42121/77; West German Patent Application (OLS) No. 2,418,959.

Examples of the suitable DIR coupler are described in such prior art references as U.S. Pat. Nos. 3,227,554; 3,617,291, 3,701,783; 3,790,384; 3,632,345, West German Patent Application (OLS) Nos. 2,414,006; 2,454,301; 2,454,329; British Patent No. 953,454; Japanese Patent Public Disclosure Nos. 69624/77; 122335/74; 69624/77; Japanese Patent Publication No. 16141/76.

The photographic sensitive material of this invention may contain a development-restrainer-releasing compound other than the DIR coupler. Suitable examples of such compound are described in U.S. Pat. Nos. 3,297,445; 3,379,529; West German Patent Application (OLS) 2,417,914.

Two or more of the above mentioned couplers may be contained in the same layer. It is also possible to have the same compound contained in two or more different layers.

These couplers may be incorporated in the silver halide emulsion layer by a conventional method of the type described in U.S. Pat. No. 2,322,027 which is the same as the method described hereinabove of incorporating the oil soluble cobalt (III) compound of this invention in the photosensitive material. When this method is used, the coupler and the oil soluble cobalt (III) compound of this invention may be contained either in the same or different particles of the emulsion, but preferably in the different particles of the emulsion.

If the coupler has an acid group such as a carboxylic acid group or sulfonic acid group, it is incorporated in a hydrophilic colloid in the form of an aqueous alkaline solution. Such coupler is contained in the emulsion layer in an amount larger than 0.375 mols (for a 4-equivalent coupler) or 0.75 mols (for a 2-equivalent coupler) per mol of silver, and preferably in an amount larger than 0.5 mols (for a 4-equivalent coupler) or 1 mol (for a 2-equivalent coupler) per mol of silver.

The "external development" wherein a color coupler of relatively low molecular weight is added to a color developing solution may be employed in this invention, but it is preferable for the purposes of this invention to use the "internal development" wherein the coupler is contained within the photosensitive material.

The coupler that can preferably be used in this invention has the following formula (V), (VI) or (VII):

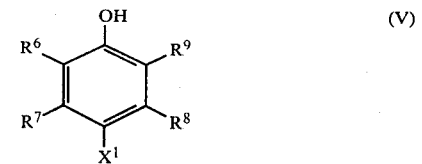
(V)

wherein $R^6$, $R^7$, $R^8$ and $R^9$ are each a hydrogen atom, a halogen atom (i.e., fluorine atom, chlorine, atom, bromine atom or iodine atom), an alkyl group (such as a methyl group, ethyl group, octyl group, dodecyl group, tetradecyl group or an octadecyl group), a carbamoyl group (such as a methyl carbamoyl group, ethyl carbamoyl group, dodecyl carbamoyl group, tetradecyl carbamoyl group, octadecyl carbamoyl group, N-phenyl carbamoyl group or N-tolyl carbamoyl group), a sulfamoyl group (such as a methyl sulfamoyl group, ethyl sulfamoyl group, dodecyl sulfamoyl group, tetradecyl sulfamoyl group, octadecyl sulfamoyl group, N-phenyl sulfamoyl group, or N-tolyl sulfamoyl group), or an amido group (such as an acetoamido group, propionamido group, benzamido group, or phenacetamido group, sulfonamido group, phosphoric acid amido group, ureido group); $R^6$ and $R^7$ may, when taken together, form a 6-membered ring (such as a phenyl group); $X^1$ is a hydrogen atom, a halogen atom (i.e., a fluorine atom, chlorine atom, bromine atom or an iodine atom) or a group releasable upon reaction with the oxidation product of the developing agent (such as an alkoxy group, aryloxy group, sulfonamido group, sulfonyl group, carbamoyl group, imido group, aminosulfonyloxy group, alkylcarbonyloxy group, arylcarbonyloxy group, alkylthio group, arylthio group, or a heterocyclic thio group); the alkyl group, carbamoyl group, sulfamoyl group or amido group represented by $R^6$, $R^7$, $R^8$ or $R^9$, or the 6-membered ring formed by $R^6$ and $R^7$ taken together may be substituted with other substituents such as an alkyl group (such as a methyl group, ethyl group, propyl group, octyl group, dodecyl group, tetradecyl group, or octadecyl group), an aryl group (such as a phenyl group, tolyl group or naphthyl group), an aryloxy group (such as a phenoxy group, 2,5-di(t)amylphenoxy group) or halogen atom (such as chlorine atom, bromine atom or fluorine atom).

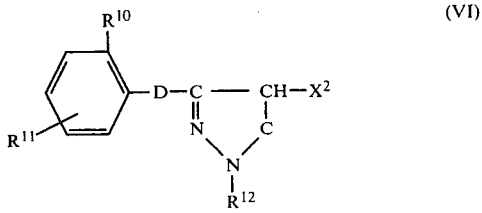

(VI)

wherein $R^{10}$ is a hydrogen atom, a halogen atom (such as a chlorine atom, bromine atom or a fluorine atom), an alkyl group (such as a methyl group, ethyl group, n-propyl group), or an alkoxy group (such as a methoxy group or ethoxy group); $R^{11}$ is an alkyl group (such as a methyl group, ethyl group, octyl group, dodecyl group, tetradecyl group or octadecyl group), an amido group (such as a butane amido group, decane amido group, tetradecane amido group or nonadecane amido group), an imido group (such as a tetradecyl succinimido group or octadecenyl succinimido group), an N-alkyl carbamoyl group (such as a decyl carbamoyl group, tetradecyl carbamoyl group, or octadecyl carbamoyl group), an N-alkyl sulfamoyl group (such as a decyl sulfamoyl group, tetradecyl sulfamoyl group or octadecyl sulfamoyl group), an alkoxycarbonyl group (such as an adesiloxycarbonyl group, tetradesiloxycarbonyl group or octadesiloxycarbonyl group), an acyloxy group (such as valeryloxy group, palmitoyloxy group, stearoyloxy group, oleoyloxy group, benzoyloxy group, or toluoyloxy group), a sulfonamido group, or urethane group; $R^{12}$ is an aryl group (such as a phenyl group or naphthyl group); D is an amino group, carbonyl amino group or ureido group; $X^2$ is a hydrogen atom, a halogen atom (such as a chlorine atom or bromine atom) or a group releasable upon reaction with the oxidation product of the developing agent (such as an arylazo group, aryloxy group, acyloxy group, alkylthio group or arylthio group); the alkyl group or alkoxy group represented by $R^{10}$, the alkyl group, amido group, N-alkyl carbamoyl group, N-alkyl sulfamoyl group, alkoxycarbonyl group or acyloxy group represented by $R^{11}$, or the aryl group represented by $R^{12}$ may be substituted with other substituents such as an alkyl group, aryl group, alkoxy group, aryloxy group, amido group, N-alkylcarbamoyl group, N-alkylsulfamoyl group, acyloxy group, carboxyl group, sulfo group or halogen atom.

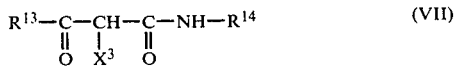

(VII)

wherein $R^{13}$ is an alkyl group (such as a methyl group, ethyl group, (t)-butyl group or (t)-octyl group), or an aryl group (such as a phenyl group); $R^{14}$ is an aryl group (such as phenyl group); $X^3$ is a hydrogen atom, a halogen atom (such as a chlorine atom or bromine atom), or a group releasable upon reaction with the oxidation product of the developing agent [such as a heterocyclic nucleus (such as a naphthoimido group, succinimido group, 5,5-dimethyl hydantoinyl group, 2,4-oxalidine dione group, imido group, pyridone group or pyridazone group), acyloxy group, sulfonyloxy group, aryloxy group or urethane group]; the alkyl group or aryl group represented by $R^{13}$ or the aryl group represented by $R^{14}$ may be substituted with other substituents such as an alkyl group, aryl group, alkoxy group, aryloxy group, amido group, N-alkylcarbamoyl group, N-alkylsulfamoyl group, acyloxy group, carboxy group, sulfo group, sulfonamido group or a halogen atom.

The photosensitive material of this invention may contain an antifoggant such as a hydroquinone derivative, aminophenol derivative, gallic acid derivative, and ascorbic acid derivative. Specific examples of the antifoggant are described in U.S. Pat. Nos. 2,360,290; 2,336,327; 2,403,721; 2,418,613; 2,675,314; 2,701,197; 2,704,713; 2,728,659; 2,732,300; 2,735,765; Japanese Patent Public Disclosure Nos. 92988/75, 92989/75; 93928/75; 110337/75; Japanese Patent Publication No. 23813/75.

The photosensitive material of this invention may contain a U.V. absorber in the layer of hydrophilic colloid. Examples of the suitable U.V. absorber are an aryl substituted benzotriazole compound (of the type described in U.S. Pat. No. 3,533,794), 4-thiazolidone compound (of the type described in U.S. Pat. Nos. 3,314,794; 3,352,681), benzophenone compound (of the type described in Japanese Patent Public Discosure No. 2784/71, cinnamate ester compound (of the type described in U.S. Pat. Nos. 3,705,805; 3,707,375), or a benzooxazole compound (of the type described in U.S. Pat. No. 2,399,762). A U.V. absorbing coupler (such as α-naphthol cyan dye forming coupler) or a U.V. absorbing polymer may also be used. These U.V. absorbers may be incorporated in a specific layer with the aid of a mordant.

The photographic sensitive material of this invention may contain an inorganic or organic hardening agent in the photographic emulsion layer or other hydrophilic colloid layers. Examples of the suitable hardening agent are a chromium salt (chromium alum or chromium acetate), an aldehyde (such as formaldehyde, glyoxal, glutaraldehyde), N-methylol compound (such as dimethylol urea, methyloldimethylhydantoin), a dioxane derivative (such as 2,3-dihydroxydioxane) an activated vinyl compound (such as 1,3,5-triacryloylhexahydro-s-triazine, bis(vinylsulfonyl)methyl ether), an activated halogen compound (such as 2,4-dichloro-6-hydroxy-s-triazine), a mucohalogenic acid (such as mucochloric acid or mucophenoxychloric acid), an isooxazole, dialdehyde starch, 2-chloro-6-hydroxytriazinylated gelatin. These hardening agents may be used independently or in combination. Specific examples of the hardening agent are described in U.S. Pat. Nos. 1,830,354; 2,080,019; 2,726,162; 2,870,013; 2,983,611; 2,992,109; 3,047,394; 3,057,723; 3,103,437; 3,321,313; 3,325,287, 3,362,827; 3,539,644; 3,543,292; British Pat. Nos. 676,628, 825,544; 1,270,578; West German Pat. Nos. 872,153; 1,090,427; Japanese Patent Publication Nos. 7133/59; 1872/71.

The photosensitive material of this invention may contain a stilbene, triazine, oxazole or coumarin brightener in the photographic emulsion layer or other hydrophilic colloid layers. These brighteners may be water soluble or dispersions containing water insoluble brighteners. Specific examples of the fluorescent brightener are described in U.S. Pat. Nos. 2,632,701; 3,269,840; 3,359,102; British Pat. Nos. 852,075; 1,319,763.

For the purposes of improving the dimensional stability and providing finer particles of emulsion, the photographic sensitive material of this invention may contain a dispersion of a water insoluble or sparingly soluble synthetic polymer in the photographic emulsion layer or other hydrophilic colloid layers. Examples of the suitable polymer are those which are composed of monomeric components such as alkyl (meth)acrylate, alkoxyalkyl (meth)acrylate, glycidyl (meth)acrylate, (meth)acrylamide, vinyl ester (such as vinyl acetate), acrylonitrile, olefin and styrene used independently or in combination, or these monomers combined with acrylic acid, methacrylic acid, $\alpha,\beta$-unsaturated dicarboxylic acid, hydroxyalkyl (meth)acrylate, sulfoalkyl (meth)acrylate, or styrene sulonic acid. Specific examples of the suitable polymer are described in U.S. Pat. Nos. 2,376,005; 2,739,137; 2,853,457; 3,062,674; 3,411,911; 3,488,708; 3,525,620; 3,607,290; 3,635,715; 3,645,740; British Pat. Nos. 1,186,699; 1,307,373.

The photosensitive material of this invention may also contain in a hydropholic colloid layer a water soluble dye as a filter dye or as means for achieving various purposes such as prevention of irradiation. Such water soluble dyes include an oxonol dye, hemioxonol dye, styryl dye, merocyanine dye, cyanine dye and azo dye. Oxonol dye, hemioxonol dye and merocyanine dye are particularly useful. Specific examples of the suitable dye are described in British Pat. Nos. 584,609; 1,177,429; Japanese Patent Public Disclosure Nos. 85130/73; 99620/74; 114420/74; U.S. Pat. Nos. 2,274,782; 2,533,472; 2,956,879; 3,148,187; 3,177,078; 3,247,127; 3,540,887; 3,575,704; 3,653,905; 3,718,472.

The photographic emulsion layer or other hydrophilic colloid layers of the sensitive material of this invention may contain various known surfactants for achieving various purposes such as easy coating, minimized static electricity, reduced slippage, uniform dispersion of emulsified particles, prevention of sticking of coated layers, and improved photographic characteristics (such as accelerated development, higher contrast and sensitization). Suitable surfactants include a nonionic surfactant such as saponin (steroid), alkylene oxide derivative (such as polyethylene glycol, polyethylene glycol/polypropylene glycol condensate, polyethylene glycol alkyl or alkyl aryl ether, polyethylene glycol sorbitan esters, polyalkylene glycol alkylamines or amides; polyethylene oxide-added silicone), glycidol alkylamines or amides; polyethylene oxide-added silicone), glycidol derivatives (such as alkenyl succinic acid polyglyceride, alkyl phenol polyglyceride), polyhydric esters of aliphatic acids, alkyl esters of sugar, urethanes or ethers of same, an anionic surfactant containing a carboxy group, a sulfo group, a phospho group, a sulfate ester group and a phosphate ester group such as triterpenoid saponin, an alkyl carboxylate, an alkyl sulfonate, an alkyl benzenesulfonate, an alkyl naphthalenesulfonate, an alkyl sulfate esters, alkyl phosphate esters, an N-acyl-N-alkyl taurines, sulfosuccinate esters, sulfoalkyl polyoxyethylene alkyl phenyl ethers, and polyoxyethylene alkyl phosphate esters; an ampholytic surfactant such as amino acids, amino alkyl sulfonic acids, amino alkyl sulfate or phosphate esters, alkyl betaines, amineimides, aminoeoxides, and a cationic surfactant such as alkyl amine salts, aliphatic or aromatic quaternary ammonium salts, heterocyclic quaternary ammonium salts such as pyridium or imidazolium, and phosphonium or sulfonium salts containing aliphatic or heterocyclic ring.

Specific examples of these surfactants are described in U.S. Pat. Nos. 2,240,742; 2,831,766; 3,158,484; 3,210,191; 3,294,540; 3,507,660; British Patent Nos. 1,012,495; 1,022,878; 1,179,290; 1,198,450; Japanese Patent Public Disclosure No. 117414/75; U.S. Pat. Nos. 2,739,891; 2,823,123; 3,068,101; 3,415,649; 3,666,478; 3,756,828; British Pat. No. 1,397,218; U.S. Patent Nos. 3,133,816; 3,441,413; 3,475,174; 3,545,974; 3,726,683; 3,843,368; Belgian Pat. No. 731,126; British Pat. Nos. 1,138,514; 1,159,825; 1,374,780; Japanese Patent Publication Nos. 378/65; 379/65; 13822/68; U.S. Patent Nos. 2,271,623; 2,288,226; 2,944,900; 3,253,919, 3,671,247; 3,772,021; 3,589,906; 3,666,478; 3,754,924; West German Patent application (OLS) No. 1,961,638; Japanese Patent Public Disclosure No. 59025/75.

The sensitive material of this invention can be processed photographically by any known method of forming a color image. One example is the "negative-positive process" (such as described in "Journal of the Society of Motion Picture and Television Engineers", Vol. 61, 1953, pp. 667-701), and another is the color reversal process wherein a developing solution containing a black-and-white developing agent is used to form a negative silver image, which is subjected to at least one uniform exposure or other suitable fogging treatment, followed by color development to provide a dye positive image.

The color developing solution generally comprises an aqueous alkaline solution containing a color developing agent, which may be any known primary aromatic amine developing agent such as phenylenediamines (for instance, 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-3-ethyl-N-$\beta$-methanesulfonamidoethylaniline, 4-amino-3-methyl-N-ethyl-N-$\beta$-methoxyethylaniline.

Other suitable developing agents are described in Photographic Processing Chemistry, by L. F. A. Mason, Focal Press, 1966, pp. 226-229, as well as in U.S. Pat. Nos. 2,193,015 and 2,592,364, and Japanese Patent Public Disclosure No. 64933/73.

The color developing solution may further contain a pH buffer such as a sulfite, carbonate, borate and phosphate of alkali metal, and a development retarder or anti-foggant such as a bromide, iodide or an organic anti-foggant. As required, the color developing solution may contain a water softener, a preservative such as hydroxylamine, an organic solvent such as benzyl alcohol or diethylene glycol, a development accelerator such as polyethylene glycol, quaternary ammonium salt or amines, a dye forming coupler, a competitive coupler, a fogging agent such as sodium borohydride, an auxiliary developing agent such as sodium borohydride, an auxiliary developing agent such as 1-phenyl-3-pyrazolidone, and a thickener.

The photographic emulsion layer as color developed is usually subjected to bleaching which may be simultaneous with or separate from fixation. Examples of the suitable bleaching agent are compounds of polyvalent metals such as iron (III), cobalt (IV), chromium (VI), and copper (II), peracids, quinones and nitroso compounds. To be more specific, ferricyanides, bichromates, organic complex salts of iron (III) or cobalt (III), such as complex salts of aminocarboxylic acids such as ethylenediaminetetraacetic acid, nitrilotriacetic acid, and 1,3-diamine-2-propanol tetraacetic acid, or organic acids such as citric acid, tartaric acid and malic acid;

persulfates, permanganates; nitrosophenol. Particularly useful are potassium ferricyanide, sodium salt of (ethylenediaminetetraaceto) iron (III) complex, and ammonium salt of (ethylenediaminetetraaceto) iron (III) complex. The (ethylenediaminetetraaceto) iron (III) complex is useful either in an independent bleaching bath or in a combined developing and fixing bath.

The bleaching bath or bleach-fix bath may contain the bleaching accelerators described in U.S. Pat. Nos. 3,042,520; 3,241,966; Japanese Patent Publication Nos. 8506/70; 8836/70, as well as other additives.

The present invention is described in more detail by the following Examples.

EXAMPLE 1

A paper support laminated with polyethylene on both sides was coated with a chlorobromide silver emulsion (silver bromide content: 50 mol%) containing an emulsion of the following composition. The resulting color paper was designated Sample (1).

| | |
|---|---|
| Gelatin (10 wt %) | 100 ml |
| Sodium dodecylbenzenesulfonate (5 wt %) | 5 ml |
| Cyan coupler | 10 g |
| 2-[α-(2,4-di-tert-amylphenoxy)butyl-amido]-4,6-dichloro-5-methylphenol (2-equivalent coupler) | |
| Dibutyl phthalate | 10 ml |
| Ethyl acetate | 10 ml |

Table 1 indicates the coating weights of silver and coupler and coupler/silver stoichiometric ratio in the color paper.

TABLE 1

| Coating Weight | Coupler | Silver |
|---|---|---|
| g/m$^2$ | 0.5 | 0.1 |
| mol/m$^2$ | 1.01 × 10$^{-3}$ | 9.3 × 10$^{-4}$ |
| Stoichiometric ratio mol %) | 217 | 100 |
| Excess coupler mol %) | 117 | — |

Separately from this color paper, an emulsion containing the cobalt (III) compound of this invention was prepared in the following manner.

A 2.5 g sample of each of the compounds I-5, I-2, I-6, I-7, II-3, III-8 and IV-6 was dissolved in a solvent comprising a mixture of 5 g of C$_{11}$H$_{23}$CON(C$_2$H$_5$)$_2$ and 15 ml of ethyl acetate, and the resulting solution was dispersed at 50° C. in 30 ml of 10 wt% gelatin containing 0.15 g of sodium dodecylbenzenesulfonate to form an emulsion.

Samples (2) to (8) were prepared by the same method as Sample (1) except that each of the above prepared emulsions was incorporated in the same silver chlorobromide emulsion. The coating weight of cobalt (III) compound for each of Samples (2) to (8) was 0.2 g/m$^2$.

As controls, Samples (9) and (10) were prepared by the same method as Sample (1) except that they contained water soluble cobalt (III) compounds [CO(NH$_3$)$_6$]Cl$_3$ and [CO(NH$_3$)$_6$][CH$_3$COO]$_3$, respectively. The coating weight of the cobalt (III) compound for both Samples (9) and (10) was 0.2 g/m$^2$.

Samples (1) to (10) were passed through a continous silver wedge, exposed to a tungsten light source having a color temperature of 2854° K., and subjected to photographic processing that comprised the steps indicated below. The photographic characteristics of each of the produced color image were measured with a Fuji autorecording densitometer, and the results are set forth in Table 2 below.

| Processing steps | Temperature | Time |
|---|---|---|
| Development | 33° C. | 3 min |
| Bleach-fix | 30° C. | 2 min |
| Water washing | 30° C. | 2 min |

| Formulation of developing solution: | |
|---|---|
| 3-Methyl-4-amino-N-ethyl-N-β-methanesulfonamidoethyl-aniline sulfate | 3 g |
| Benzyl Alcohol | 10 g |
| Sodium sulfite | 2.5 g |
| Potassium Bromide | 0.2 g |
| Sodium Carbonate (monohydrate) | 30 g |
| Sodium Hydroxide | 0.2 g |
| Water to make | 1 l |

| Bleach-fix bath: | |
|---|---|
| Ammonium Thiosulfate | 100 g |
| Sodium Salt of (ethylenediaminetetraaceto) iron (III) complex | 50 g |
| Disodium Ethylenediaminetetraacetate | 5 g |
| Sodium Sulfite | 10 g |
| Water to make | 1 l |

TABLE 2

| Sample | Cobalt (III) Compound | Maximum Density (Dmax) | Relative Sensitivity* |
|---|---|---|---|
| 1 | None | 1.50 | 0 |
| 2 | I-5 | 1.81 | −1.3 |
| 3 | I-2 | 1.92 | −0.9 |
| 4 | I-6 | 1.80 | −1.1 |
| 5 | I-7 | 1.93 | −1.2 |
| 6 | II-3 | 1.79 | −1.0 |
| 7 | III-8 | 1.75 | −0.8 |
| 8 | IV-6 | 1.60 | −0.7 |
| 9 | [Co(NH$_3$)$_6$]Cl$_3$ | 1.80 | −2.5 |
| 10 | [Co(NH$_3$)$_6$][CH$_3$COO]$_3$ | 1.93 | −2.1 |

*Sensitivity (in logarithms) relative to the absence of cobalt (III) compound which is assumed to have zero sensitivity.

As Table 2 shows, the samples containing cobalt (III) compounds had a higher Dmax than Sample (1) containing no such cobalt compound, but Samples (9) and (10) containing cobalt compounds other than those defined in this invention provided markedly lower relative sensitivities than Samples (2) to (8) that incorporated the cobalt compound of this invention.

EXAMPLE 2

Five paper supports each laminated with polyethylene on both sides were coated with gelatin layers containing emulsions having the cobalt (III) compounds II-4, I-2, III-8, I-7 and IV-6, of this invention, respectively, prepared in the same manner as in Example 1, then coated with a gelatin intermediate layer (coating weight of gelatin: 1.0 g/m$^2$) which was overlaid with a silver chlorobromide emulsion (silver bromide content: 50 mol%) containing an emulsion of magenta coupler of the following formulation. The resulting color papers were designated Samples (12) to (16).

As controls, Sample (11) was prepared which had a coating of gelatin layer free from an emulsion of cobalt (III) compound, and Sample (17) was prepared which had a coating of gelatin layer containing a water soluble cobalt (III) compound other than those specified in this invention.

| Formulation of emulsion: | |
|---|---|
| Gelatin (10 wt %) | 100 ml |
| Sodium Dodecylbenzene-sulfonate (5 wt %) | 5 ml |
| Magenta Coupler 1-[2,4,6-trichlorophenyl)-3-(2-chloro-5-tetradecaneamido)-anilino]-5-pyrazolone | 10 g |
| Dibutyl Phthalate | 10 ml |
| Ethyl Acetate | 10 ml |

Table 3 indicates the coating weights of silver and coupler and coupler/silver stoichiometric ratio in the color paper.

TABLE 3

| Coating Weight | Coupler | Silver |
|---|---|---|
| g/m$^2$ | 0.4 | 0.1 |
| mol/m$^2$ | $6.5 \times 10^{-4}$ | $9.3 \times 10^{-4}$ |
| Stoichiometric ratio (mol %) | 279 | 100 |
| Excess coupler mol %) | 179 | — |

Samples (11) to (17) were subjected to a 2-day forced ageing test at 40° C. and 78% RH, exposed and developed as in Example 1, and the resulting images were evaluated for the sensitivities of the samples by measurement of their densities with an auto-recording densitometer. The results are indicated in Table 4 below.

TABLE 4

| Sample | Cobalt (III) Compound | Maximum Density (Dmax) | Relative Sensitivity | Desensitization by forced ageing test |
|---|---|---|---|---|
| 11 | None | 1.20 | 0 | −0.18 |
| 12 | II-4 | 1.68 | −0.7 | −0.48 |
| 13 | I-2 | 1.72 | −0.6 | −0.67 |
| 14 | III-8 | 1.65 | −0.6 | −0.42 |
| 15 | I-7 | 1.78 | −0.7 | −0.27 |
| 16 | IV-6 | 1.55 | −0.6 | −0.45 |
| 17 | [Co(NH$_3$)$_6$][CH$_3$COO] | 1.53 | −1.6 | −0.67 |

As Table 4 shows, the samples containing the compounds of the formulae (I), (II), (III) and (IV) of this invention provided higher Dmax, higher relative sensitivities, and less decrease in sensitivity following a forced ageing test than Sample (11) free from cobalt (III) compound as well as Sample (17) containing a cobalt (III) other than the cobalt (III) compound of this invention.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support and at least one silver halide emulsion layer, at least one layer of said photographic material containing at least one compound selected from the group consisting of those compounds represented by the formulae (I), (II), (III) and (IV):

$$[Co(NH_3)_6][R^1COO]_3 \quad (I)$$

$$[Co(NH_3)_6][R^2OOCR^3COO]_3 \quad (II)$$

$$[Co(NH_3)_5(R^4COO)]X_2 \quad (III)$$

$$[Co(NH_3)_5(R^5NH_2)]X_3 \quad (IV)$$

wherein R$^1$, R$^2$ and R$^4$ each represent an alkyl group having at least 3 carbon atoms or a fluorine-substituted alkyl group having at least 1 carbon atom; R$^3$ is an alkylene group; R$^5$ is an alkyl group having at least 1 carbon atom; and X is a halogen atom, a nitrate ion, a sulfate ion, or a carboxylate ion, wherein said at least one compound is within an oil-in-water emulsion.

2. The color photographic material of claim 1, wherein R$^1$, R$^2$ or R$^4$ is an unsubstituted alkyl group having 3 to 20 carbon atoms.

3. The color photographic material of claim 1, wherein R$^3$ is an alkylene chain having 1 to 10 carbon atoms.

4. The color photographic material of claim 1, wherein R$^5$ is an alkyl group having 1 to 20 carbon atoms.

5. The color photographic material of claim 1, wherein the compound represented by the formula (I), (II), (III) or (IV) is present in an amount in the range of from about 0.01 to about 10 mols per mol of silver halide.

6. The color photographic material of claim 1, wherein said color photographic material contains a coupler in at least 50 mol% excess of the amount stoichiometrically required based on the amount of silver.

7. The color photographic material of claim 1, wherein said color photographic material contains less than about 1 g/m$^2$ of silver per layer.

8. The color photographic material of claim 1, wherein the cobalt (III) compound represented by the formula (I), (II), (III) or (IV) is present within particles of said oil-in-water emulsion in said silver halide emulsion layer and said emulsion is substantially coupler-free.

9. The color photographic material of claim 1, wherein the cobalt (III) compound represented by the formula (I), (II), (III) or (IV) is present within particles of said oil-in-water emulsion which is in a non-sensitive hydrophilic colloid layer adjacent a silver halide emulsion layer.

10. The color photographic material of claim 1, wherein the cobalt (III) compound represented by the formula (I), (II), (III) or (IV) is present within particles of said oil-in-water emulsion which is in a non-sensitive hydrophilic colloid layer adjacent to a non-sensitive hydrophilic colloid layer adjacent a silver halide emulsion layer.

11. The color photographic material of claim 1, wherein the cobalt (III) compound represented by the formula (I), (II), (III) or (IV) is present within particles of said oil-in-water emulsion in an organic solvent having a boiling point higher than about 180° C.

12. The color photographic material of claim 1, wherein said layer containing said cobalt compound-containing layer is located between the silver halide emulsion layer and the support.

13. The color photographic material of claim 12, wherein said cobalt compound-containing layer is adjacent the silver halide emulsion layer.

14. The color photographic material of claim 12, wherein a non light-sensitive layer is interposed between the cobalt compound-containing layer and the silver halide emulsion layer.

15. The color photographic material of claim 1, wherein said material is a color paper.

16. The color photographic material of claim 15, wherein said support is paper coated on one or both sides with a polyolefin.

17. The color photographic material of claim 1, wherein the cobalt (III) compound represented by formulae (I), (II), (III) or (IV) is present within said oil-in-water emulsion dispersed in said silver halide emulsion or a hydrophilic colloid of at least one layer of said photographic material.

18. A image forming process which comprises imagewise exposing and developing the color photographic material of claim 1 using a color developer in the presence of a color developing agent.

19. The process of claim 18, wherein said material is developed by a negative-positive process.

20. The process of claim 18, wherein said material is developed by a color reversal process which comprises developing said material with a black-and-white developer, fogging, and color developing.

* * * * *